United States Patent
Chen

(10) Patent No.: US 12,226,350 B1
(45) Date of Patent: Feb. 18, 2025

(54) SLEEPING EYESHADE

(71) Applicant: Shuying Chen, Shaoxing (CN)

(72) Inventor: Shuying Chen, Shaoxing (CN)

( * ) Notice: Subject to any disclaimer, the term of this patent is extended or adjusted under 35 U.S.C. 154(b) by 0 days.

(21) Appl. No.: 18/660,843

(22) Filed: May 10, 2024

(30) Foreign Application Priority Data

Apr. 29, 2024 (CN) .......................... 202420923155.1

(51) Int. Cl.
*A61F 9/04* (2006.01)

(52) U.S. Cl.
CPC .................................... *A61F 9/045* (2013.01)

(58) Field of Classification Search
CPC ........................... A41D 13/11; A41D 13/1161; A41D 13/1184; A41F 1/006; A61F 9/02; A61F 9/027; A61F 9/04; A61F 9/045; A63B 33/002; A63B 33/004
See application file for complete search history.

(56) References Cited

U.S. PATENT DOCUMENTS

| | | | | |
|---|---|---|---|---|
| 1,924,315 A * | 8/1933 | Hemphill | ................. | A61F 9/04 D24/189 |
| 2,305,080 A * | 12/1942 | Hemphill | ................. | A61F 9/04 2/15 |
| 2,671,898 A * | 3/1954 | Wade | ...................... | A61F 9/027 128/858 |
| 4,872,217 A * | 10/1989 | Kitayama | ................. | A61F 9/04 2/15 |
| 5,046,200 A * | 9/1991 | Feder | ................... | A63B 33/002 2/452 |
| 6,820,615 B1 * | 11/2004 | Feng | ...................... | B63C 11/12 2/430 |
| 9,572,718 B2 * | 2/2017 | Sternlight | ............... | A61F 11/12 |
| 10,624,788 B2 * | 4/2020 | Lazor | ........................ | A61F 9/04 |
| 10,646,377 B2 * | 5/2020 | Schwarz | ................. | A61F 9/045 |
| 2013/0139305 A1 * | 6/2013 | Rao | ....................... | A63B 33/004 2/452 |
| 2016/0008175 A1 * | 1/2016 | Bergman | .................. | A61F 9/04 2/171.2 |
| 2019/0133827 A1 * | 5/2019 | Carver | ....................... | A61F 9/04 |
| 2019/0231595 A1 * | 8/2019 | Holtz | ......................... | A61F 9/04 |
| 2023/0000188 A1 * | 1/2023 | Dubois | ..................... | A61F 9/04 |

* cited by examiner

*Primary Examiner* — F Griffin Hall

(57) ABSTRACT

A sleeping eyeshade includes an eyeshade main body, an elastic tightening strap component, and a flexible anti-slip pad body. The eyeshade main body is equipped with a first end and a second end. One end of the tightening strap component is connected to the first end, and an opposite end of the tightening strap component is connected to the second end. The flexible anti-slip pad body is connected to the tightening strap component, and a tightening space is surrounded and formed among the flexible anti-slip pad body, the tightening strap component, and the eyeshade main body. Therefore, when a user is using the sleeping eyeshade, the eyeshade main body can be tightly tied to the user's head through the tightening space. Moreover, since the flexible anti-slip pad body is equipped, the flexible anti-slip pad body can be used to fit the user's head.

15 Claims, 11 Drawing Sheets

SLEEPING EYESHADE

CROSS-REFERENCE TO RELATED APPLICATIONS

The application claims priority of Chinese patent application CN2024209231551, filed on Apr. 29, 2024, which is incorporated herein by reference in its entireties.

TECHNICAL FIELD

The present invention relates to a field of eyeshades, in particular to a sleeping eyeshade.

BACKGROUND ART

For some people who are sensitive to light, the stimulation of light can greatly affect their sleep quality. For example, during the day or during long-distance travel on airplanes, cars, and ships, there may be interference and stimulation from light, which greatly affects the sleep quality of users. Therefore, there is an urgent need to provide a sleeping eyeshade on the market to reduce light interference and improve the sleep quality of users.

SUMMARY

In order to overcome the shortcomings of the prior art, a sleeping eyeshade is provided in the present invention, including: an eyeshade main body, the eyeshade main body being equipped with a first end and a second end; an elastic tightening strap component, one end of the tightening strap component being connected to the first end, and an opposite end of the tightening strap component being connected to the second end; and a flexible anti-slip pad body, the flexible anti-slip pad body being connected to the tightening strap component, and a tightening space being surrounded and formed among the flexible anti-slip pad body, the tightening strap component, and the eyeshade main body.

As an improvement of the present invention, the sleeping eyeshade further includes an adjustment component. The adjustment component is connected to the tightening strap component for adjusting a size of the tightening space.

As an improvement of the present invention, the tightening strap component includes a first tightening strap and a second tightening strap. The flexible anti-slip pad body is equipped with a seventh end and an eighth end. The seventh end of the flexible anti-slip pad body is connected to the first end via the first tightening strap, and the eighth end of the flexible anti-slip pad body is connected to the second end via the second tightening strap.

As an improvement of the present invention, the adjustment component includes a first adjustment buckle. The first adjustment buckle is provided with a first main body and a first partition part. The first main body is provided with a first upper surface, a first lower surface, and a first opening. The first partition part is connected to the first main body. The first partition part is configured for separating the first opening into a first adjustment hole and a second adjustment hole. The seventh end is provided with a third adjustment hole. The first tightening strap is equipped with a third end and a fourth end. The first adjustment buckle is positioned between the third end and the fourth end. The third end is connected to the first end. The fourth end passes through the first adjustment hole from the first lower surface of the first main body to enter the first upper surface, then sequentially passes through the first partition part and the second adjustment hole from the first upper surface to enter the first lower surface, and finally sequentially passes through the third adjustment hole and the first lower surface to connect with the first partition part, so that the first tightening strap is slidable on the first partition part to adjust a distance between the first end and the seventh end, thereby adjusting the size of the tightening space.

As an improvement of the present invention, the adjustment component includes a second adjustment buckle. The second adjustment buckle is equipped with a second main body and a second partition part. The second main body is provided with a second upper surface, a second lower surface, and a second opening. The second partition part is connected to the second main body, and the second partition part is configured for separating the second opening into a fourth adjustment hole and a fifth adjustment hole. The eighth end is provided with a sixth adjustment hole. The second tightening strap is provided with a fifth end and a sixth end. The second adjustment buckle is positioned between the fifth end and the sixth end. The fifth end is connected to the second end. The sixth end passes through the fourth adjustment hole from the second lower surface of the second main body to enter the second upper surface, then sequentially passes through the second partition part and the fifth adjustment hole from the second upper surface to enter the second lower surface, and finally sequentially passes through the sixth adjustment hole and the second lower surface to connect with the second partition part, so that the second tightening strap is slidable on the second partition part to adjust a distance between the second end and the eighth end, thereby adjusting the size of the tightening space.

As an improvement of the present invention, the seventh end is provided with a first convex lug part, and the eighth end is provided with a second convex lug part. The third adjustment hole is defined in the first convex lug part, and the sixth adjustment hole is defined in the second convex lug part.

As an improvement of the present invention, the sleeping eyeshade further includes a first installation buckle and a second installation buckle. The first installation buckle is connected to the seventh end, and the second installation buckle is connected to the eighth end. The third adjustment hole is defined in the first installation buckle, and the sixth adjustment hole is defined in the second installation buckle.

As an improvement of the present invention, the fourth end is equipped with a first sleeving opening. The first sleeving opening wraps the first partition part to connect the fourth end with the first partition part. The sixth end is equipped with a second sleeving opening. The second sleeving opening wraps the second partition part to connect the sixth end with the second partition part.

As an improvement of the present invention, the first tightening strap and the second tightening strap extend longitudinally, and a transverse width of the flexible anti-slip pad body is greater than a transverse width of the first tightening strap and the second tightening strap.

As an improvement of the present invention, the flexible anti-slip pad body is a flexible TPE anti-slip pad body.

As an improvement of the present invention, the flexible anti-slip pad body is a flexible silicone anti-slip pad body.

As an improvement of the present invention, the flexible anti-slip pad body is a flexible cloth anti-slip pad body.

As an improvement of the present invention, an inner side of the eyeshade main body is provided with a first concavity and a second concavity. The first concavity and the second concavity are respectively positioned on a left side and a right side of the eyeshade main body. The first concavity and the second concavity are configured for avoiding a user's eyes.

As an improvement of the present invention, the inner side of the eyeshade main body is further provided with a third concavity. The third concavity is positioned between the first concavity and the second concavity. The third concavity is configured for avoiding an area between eyebrows.

As an improvement of the present invention, a lower side of the eyeshade main body is further provided with a first avoidance gap. The first avoidance gap is configured for avoiding a nose.

As an improvement of the present invention, a lower side of the third concavity extends to the first avoidance gap, and the third concavity is provided with a channel. The third concavity is in communication with the first avoidance gap through the channel.

As an improvement of the present invention, the first end of the eyeshade main body is equipped with a third convex lug part, and the second end of the eyeshade main body is equipped with a fourth convex lug part. The third end of the first tightening strap is connected to the third convex lug part, and the fifth end of the second tightening strap is connected to the fourth convex lug part.

As an improvement of the present invention, the third end is connected to the first end by stitching, and the fifth end is connected to the second end by stitching.

As an improvement of the present invention, the eyeshade main body includes an outer layer, an inner layer, and a light shading filling layer. The outer layer is connected to the inner layer, and an accommodating cavity is formed between the inner layer and the outer layer. The light shading filling layer is positioned inside the accommodating cavity.

The sleeping eyeshade is provided in the present invention, including the eyeshade main body, the elastic tightening strap component, and the flexible anti-slip pad body. The eyeshade main body is equipped with the first end and the second end. One end of the tightening strap component is connected to the first end, and an opposite end of the tightening strap component is connected to the second end. The flexible anti-slip pad body is connected to the tightening strap component, and the tightening space is surrounded and formed among the flexible anti-slip pad body, the tightening strap component, and the eyeshade main body. Therefore, when the user is using the sleeping eyeshade, the eyeshade main body can be tightly tied to the user's head through the tightening space surrounded and formed among the flexible anti-slip pad body, the tightening strap component, and the eyeshade main body. Since the flexible anti-slip pad body is equipped, the flexible anti-slip pad body can be used to fit the user's head. By increasing a friction force between the flexible anti-slip pad body and the head, a tightening force of the tightening space can be enhanced to prevent the eyeshade from slipping off the user's head. Moreover, the flexible anti-slip pad body is capable of reducing the pressure on the head to improve the user's wearing comfort.

BRIEF DESCRIPTION OF THE DRAWINGS

Implementations of the present disclosure will now be described, by way of embodiment, with reference to the attached figures. It should be understood, the drawings are shown for illustrative purpose only, for ordinary person skilled in the art, other drawings obtained from these drawings without paying creative labor by an ordinary person skilled in the art should be within scope of the present disclosure.

DETAILED DESCRIPTION OF THE EMBODIMENTS

Figure 1:
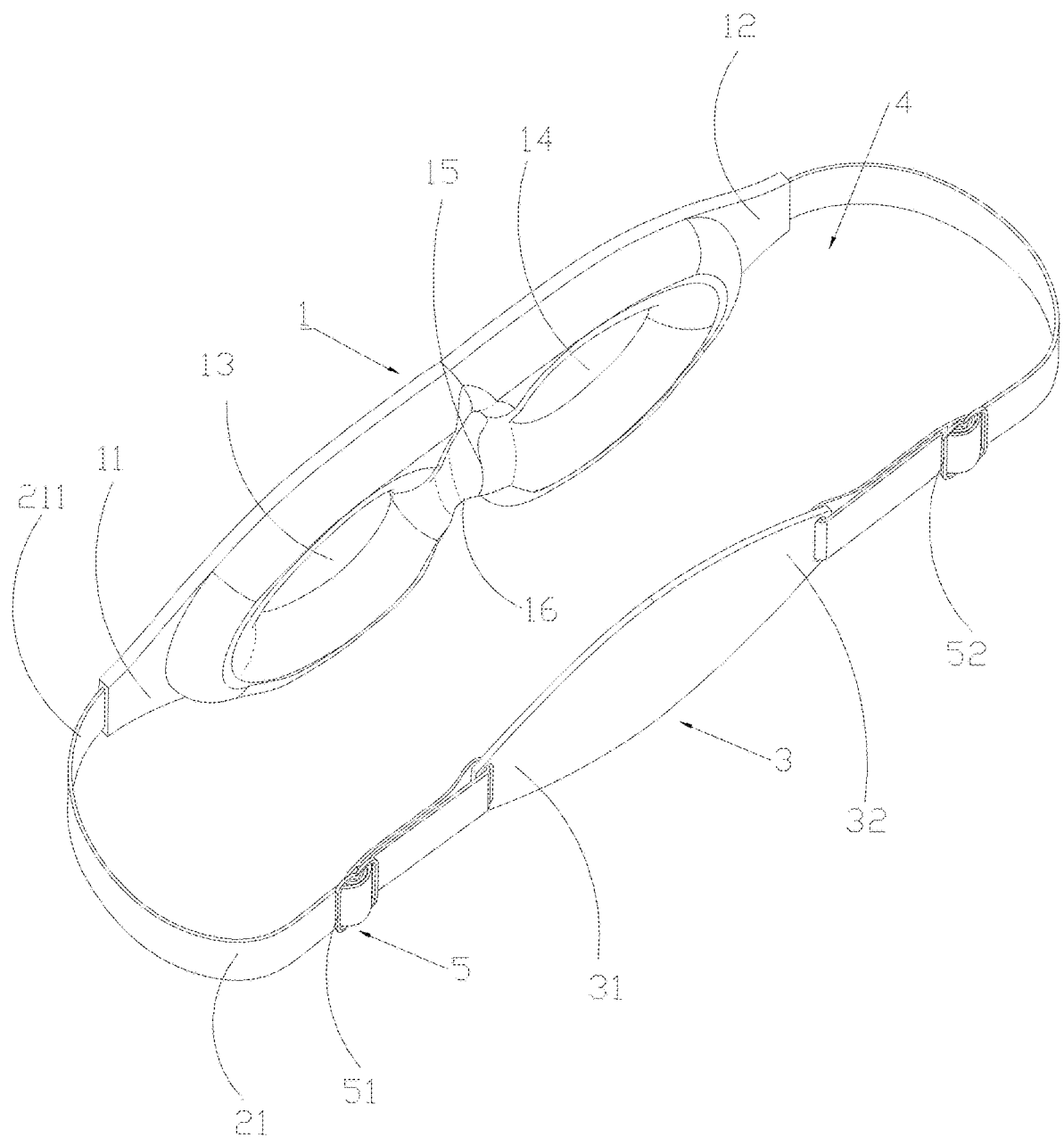
FIG. 1 is a schematic diagram of an overall structure according to the present invention.
Figure 2:
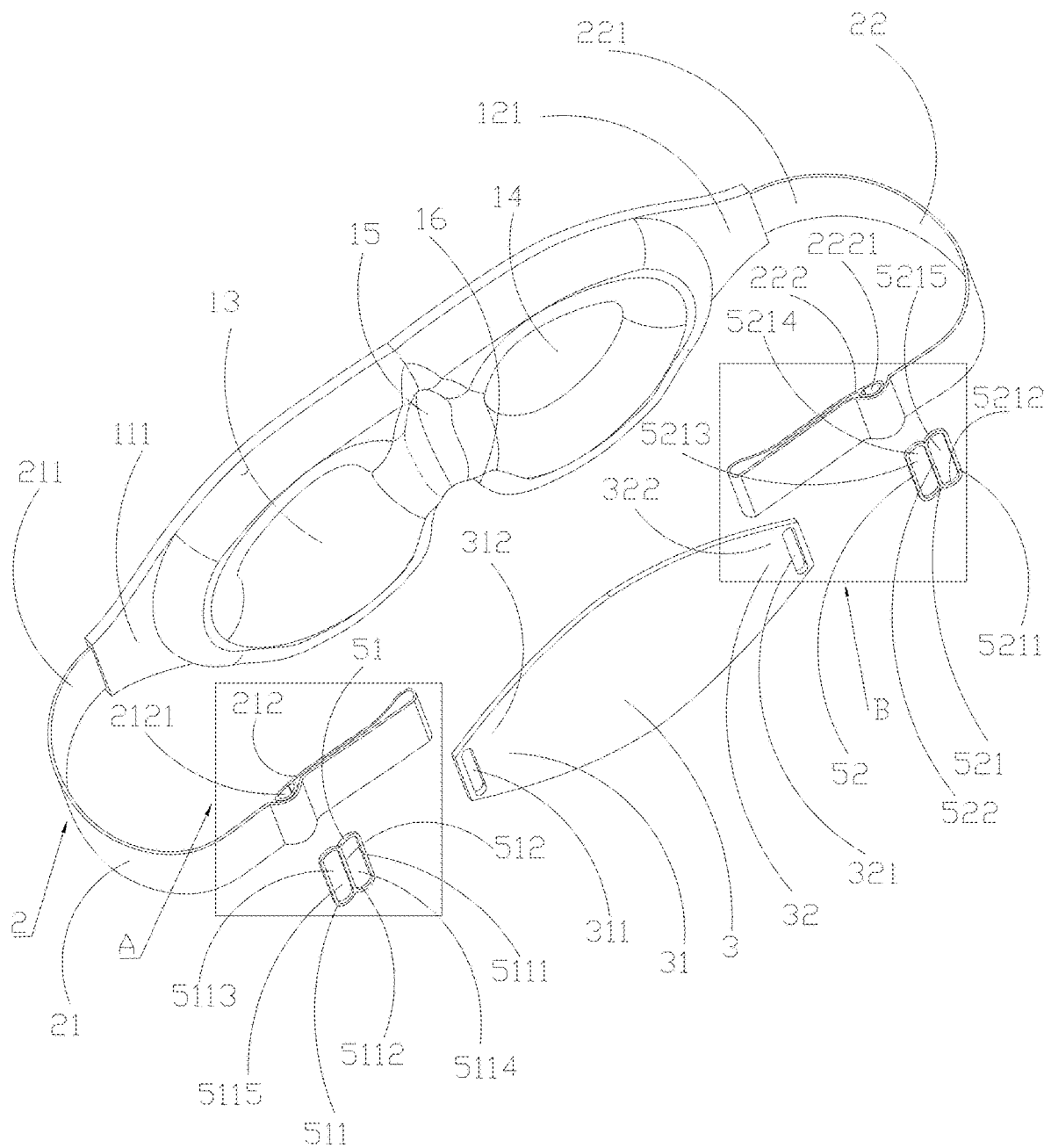
FIG. 2 is an exploded view according to the present invention.
Figure 3:
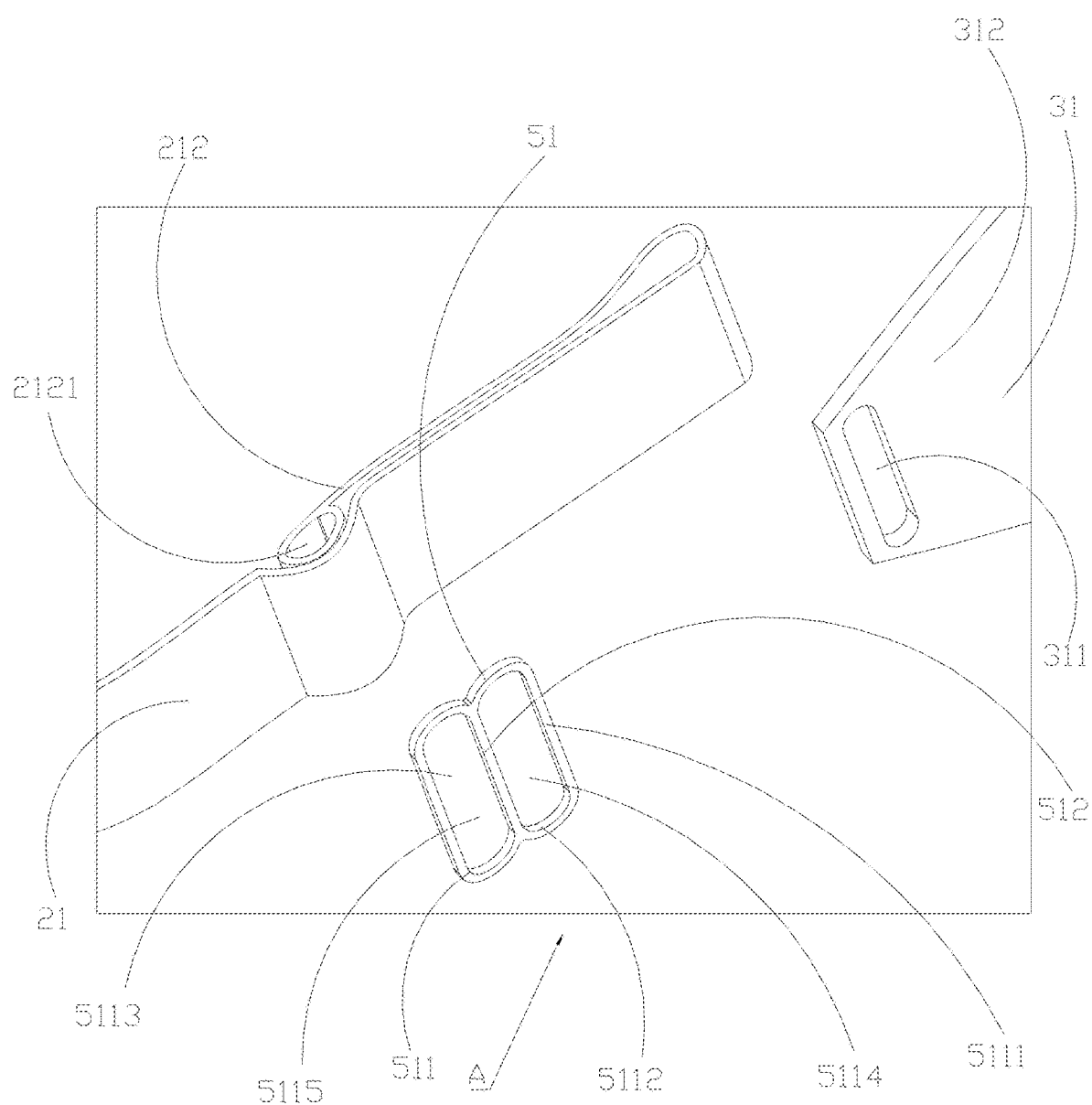
FIG. 3 is an enlarged view of area A in FIG. 2.
Figure 4:
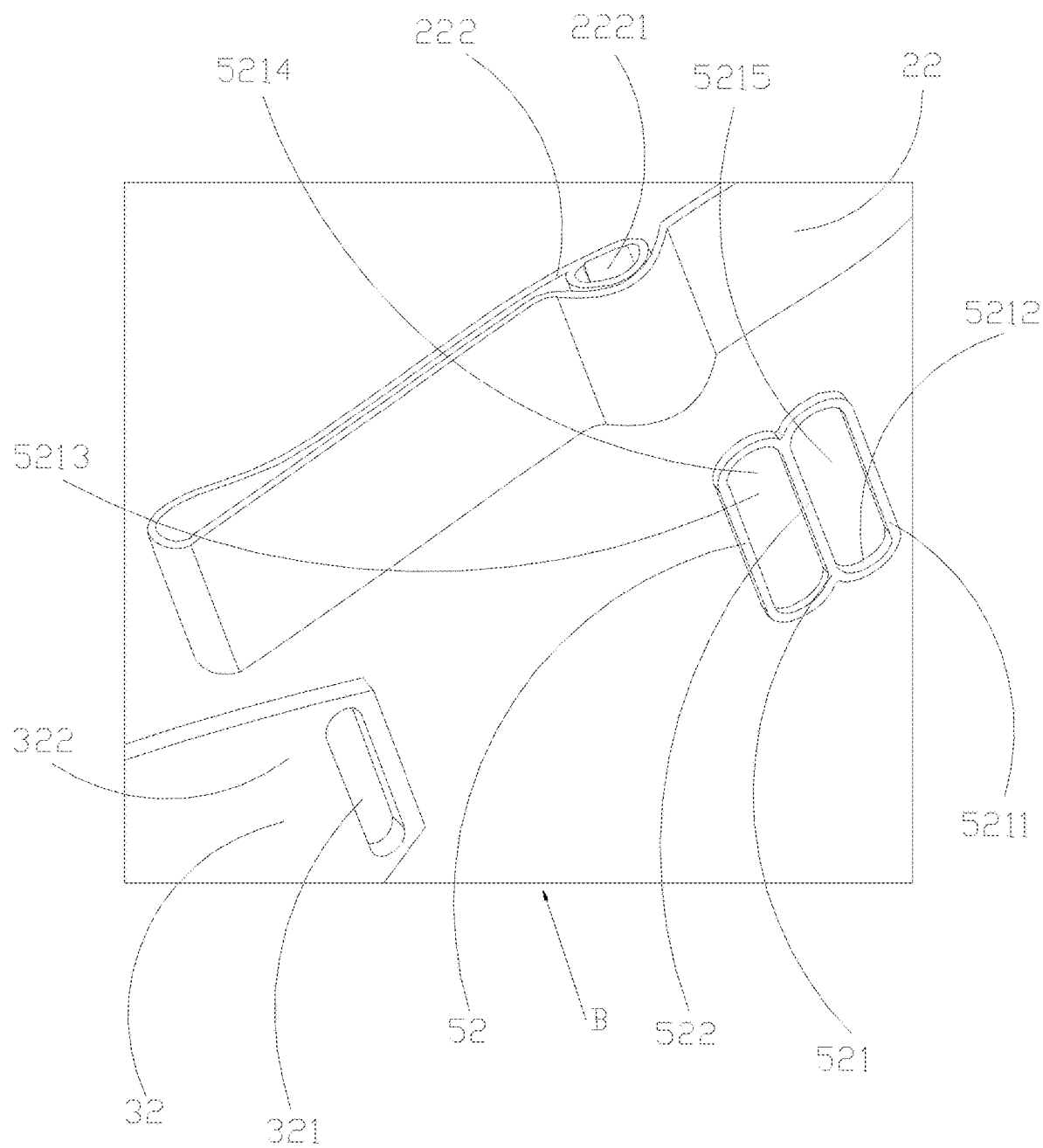
FIG. 4 is an enlarged view of area B in FIG. 2.
Figure 5:
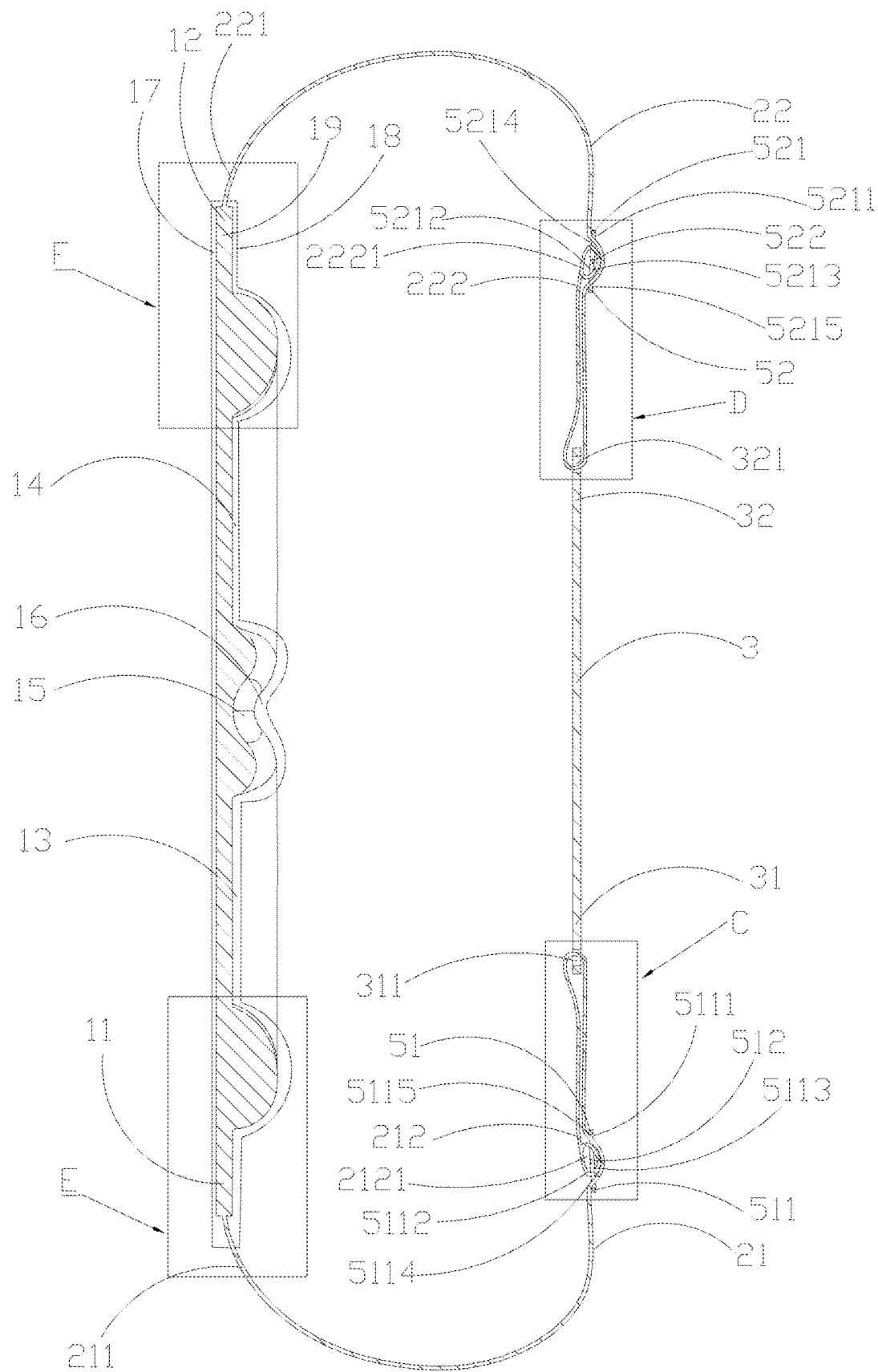
FIG. 5 is a sectional view of an eyeshade main body, a first tightening strap, a second tightening strap, and a flexible anti-slip pad body.
Figure 6:
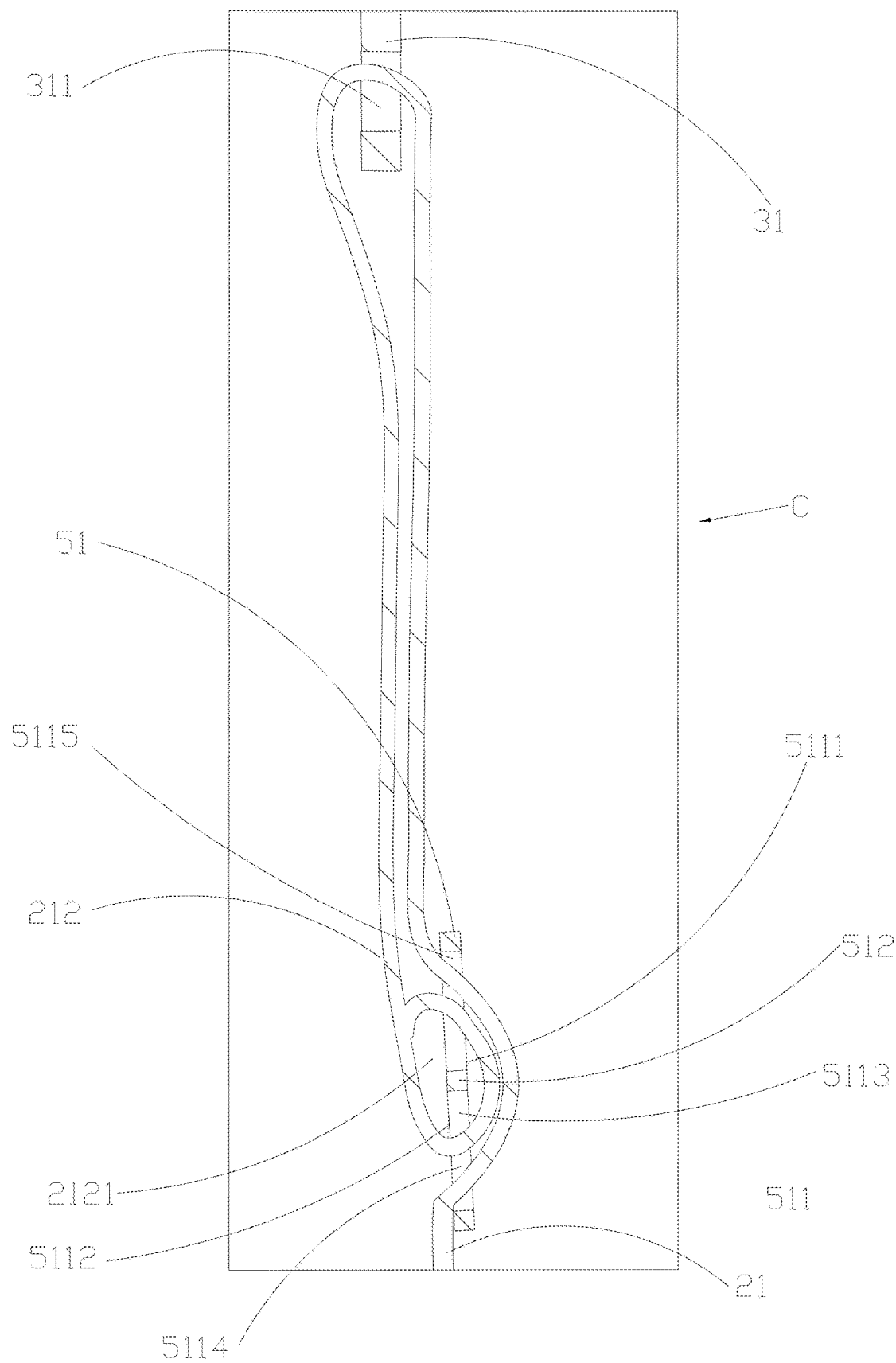
FIG. 6 is an enlarged view of area C in FIG. 5.
Figure 7:
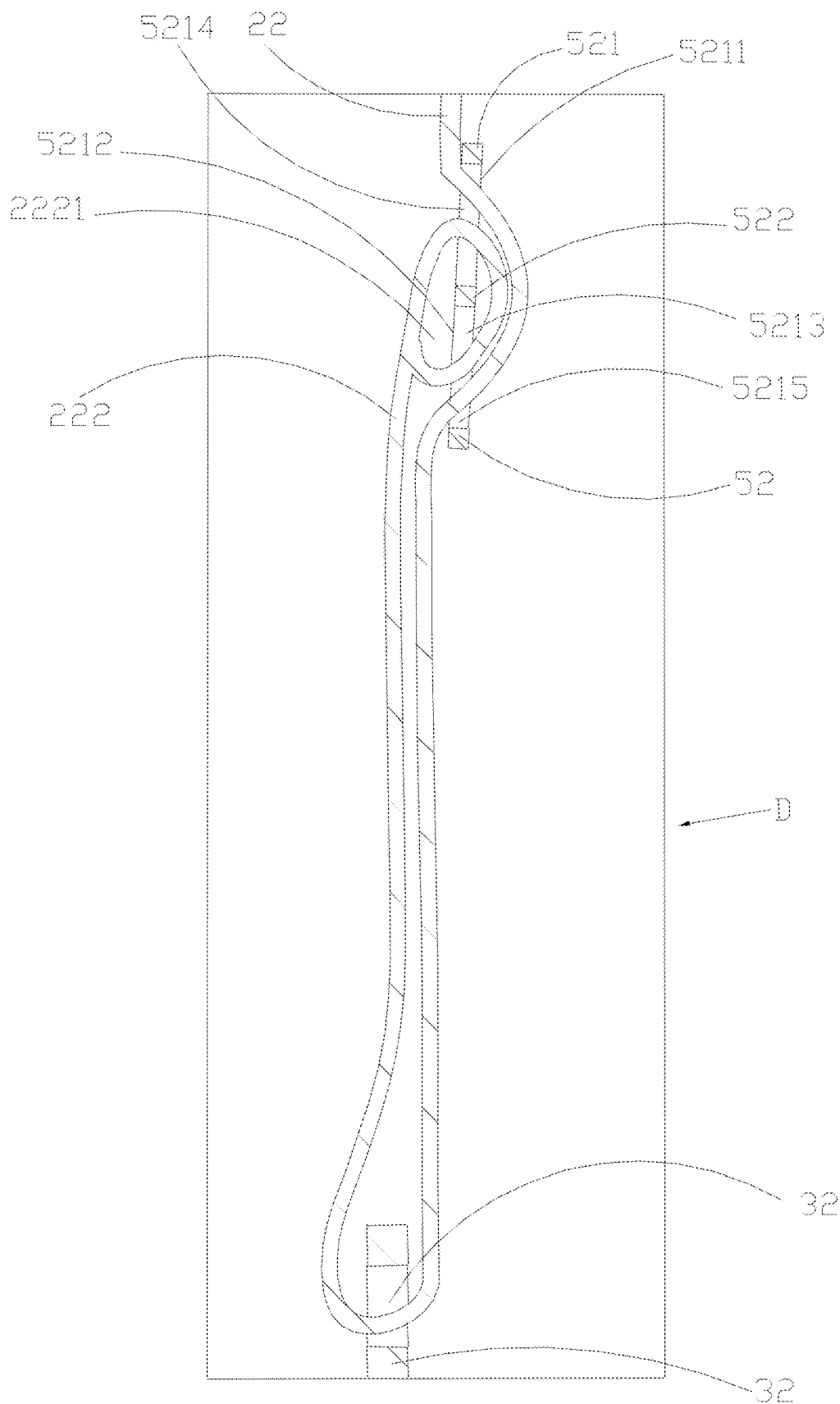
FIG. 7 is an enlarged view of area D in FIG. 5.
Figure 8:
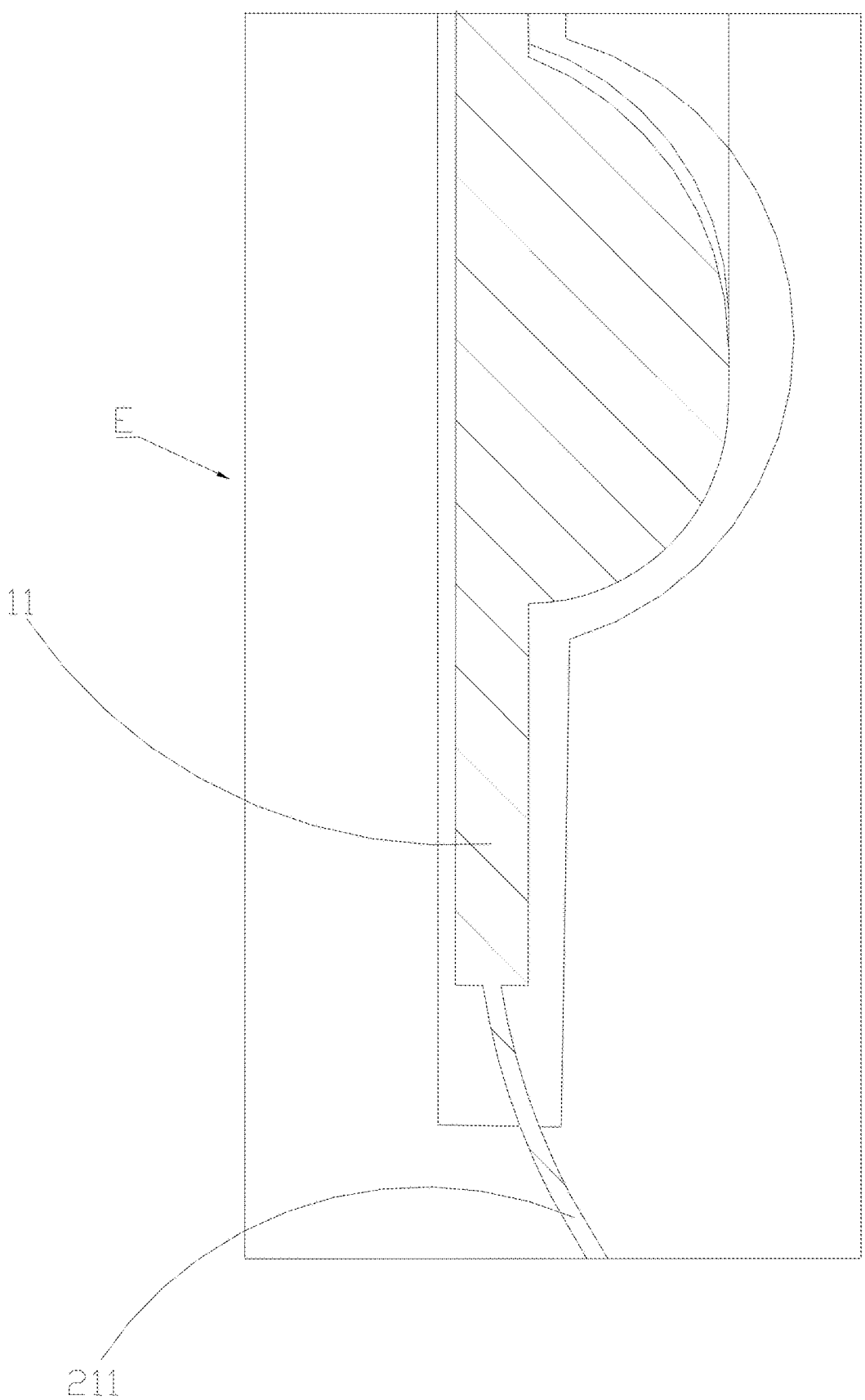
FIG. 8 is an enlarged view of area E in FIG. 5.
Figure 9:
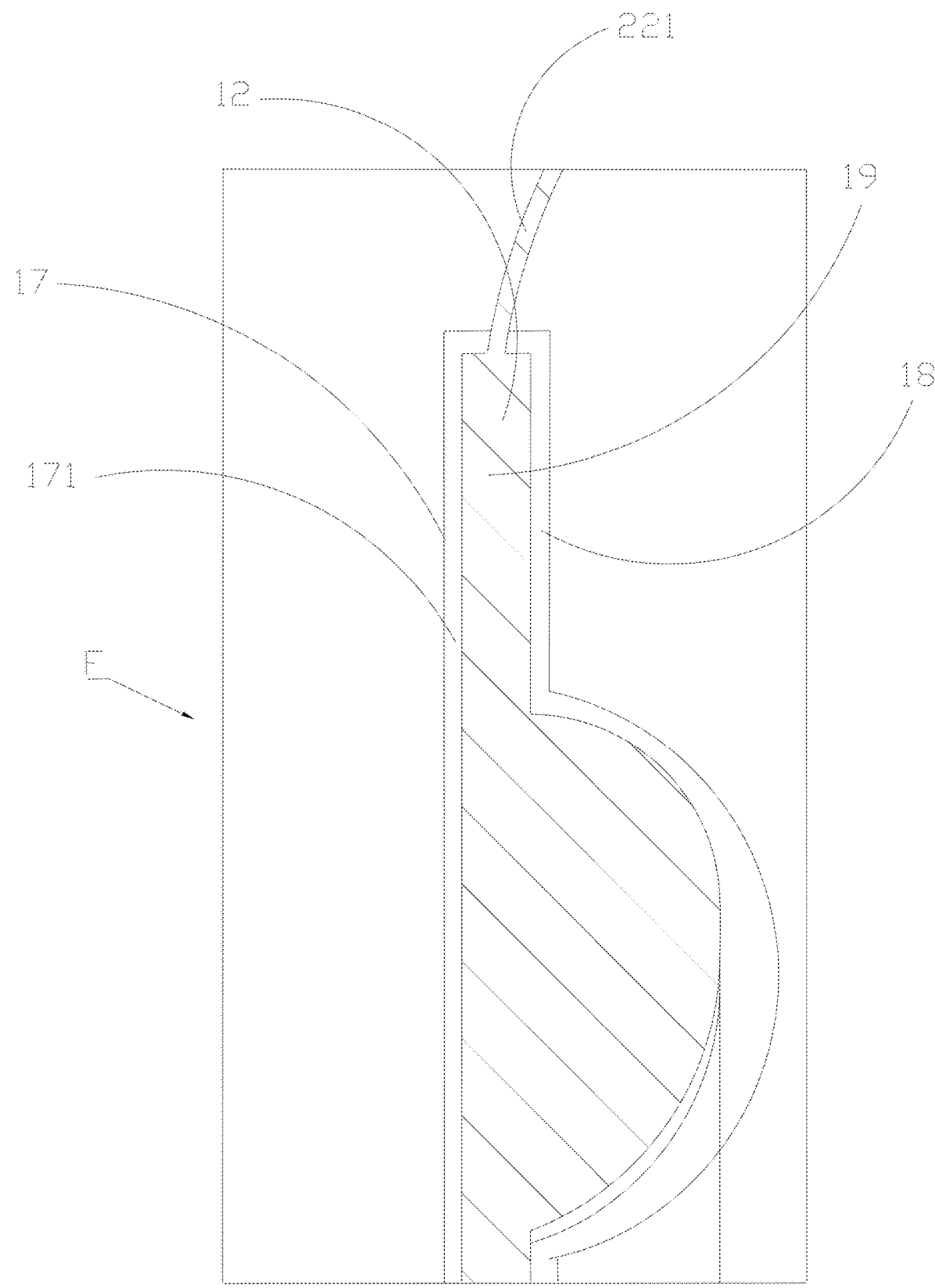
FIG. 9 is an enlarged view of area F in FIG. 5.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the features. In the description of embodiments of the application, "a plurality of" means two or more, unless otherwise specifically defined.

Referring to FIGS. 1-9, a sleeping eyeshade includes: an eyeshade main body 1, the eyeshade main body 1 being equipped with a first end 11 and a second end 12; an elastic tightening strap component 2, one end of the tightening strap component 2 being connected to the first end 11, and an opposite end of the tightening strap component 2 being connected to the second end 12; and a flexible anti-slip pad body 3, the flexible anti-slip pad body 3 being connected to the tightening strap component 2, and a tightening space 4 being surrounded and formed among the flexible anti-slip pad body 3, the tightening strap component 2, and the eyeshade main body 1.

Through the above structure, the sleeping eyeshade includes the eyeshade main body 1, the elastic tightening strap component 2, and the flexible anti-slip pad body 3. The eyeshade main body 1 is equipped with a first end 11 and a second end 12. One end of the tightening strap component 2 is connected to the first end 11, and an opposite end of the tightening strap component 2 is connected to the second end 12. The flexible anti-slip pad body 3 is connected to the tightening strap component 2, and the tightening space 4 is surrounded and formed among the flexible anti-slip pad body 3, the tightening strap component 2, and the eyeshade main body 1. Therefore, when a user is using the sleeping eyeshade, the eyeshade main body 1 can be tightly tied to the user's head through the tightening space 4 surrounded and formed among the flexible anti-slip pad body 3, the tightening strap component 2 and the eyeshade main body 1. Since the flexible anti-slip pad body 3 is equipped, the flexible anti-slip pad body 3 can be used to fit the user's head. By increasing a friction force between the flexible anti-slip pad body 3 and the head, a tightening force of the tightening space 4 can be enhanced to prevent the eyeshade from slipping off the user's head. Moreover, the flexible anti-slip pad body 3 is capable of reducing the pressure on the head to improve the user's wearing comfort.

In this embodiment, the sleeping eyeshade further includes an adjustment component 5. The adjustment component 5 is connected to the tightening strap component 2 for adjusting a size of the tightening space 4. The tightening strap component 2 includes a first tightening strap 21 and a second tightening strap 22. The flexible anti-slip pad body 3 is equipped with a seventh end 31 and an eighth end 32. The seventh end 31 of the flexible anti-slip pad body 3 is connected to the first end 11 via the first tightening strap 21, and the eighth end 32 of the flexible anti-slip pad body 3 is connected to the second end 12 via the second tightening strap 22. Specifically, the adjustment component 5 includes a first adjustment buckle 51. The first adjustment buckle 51 is provided with a first main body 511 and a first partition part 512. The first main body 511 is provided with a first upper surface 5111, a first lower surface 5112, and a first opening 5113. The first partition part 512 is connected to the first main body 511. The first partition part 512 is configured for separating the first opening 5113 into a first adjustment hole 5114 and a second adjustment hole 5115. The seventh end 31 is provided with a third adjustment hole 311. The first tightening strap 21 is equipped with a third end 211 and a fourth end 212. The first adjustment buckle 51 is positioned between the third end 211 and the fourth end 212. The third end 211 is connected to the first end 11. The fourth end 212 passes through the first adjustment hole 5114 from the first lower surface 5112 of the first main body 511 to enter the first upper surface 5111, then sequentially passes through the first partition part 512 and the second adjustment hole 5115 from the first upper surface 5111 to enter the first lower surface 5112, and finally sequentially passes through the third adjustment hole 311 and the first lower surface 5112 to connect with the first partition part 512, so that the first tightening strap 21 is capable of sliding on the first partition part 512 to adjust a distance between the first end 11 and the seventh end 31, thereby adjusting the size of the tightening space 4. Furthermore, the adjustment component 5 includes a second adjustment buckle 52. The second adjustment buckle 52 is equipped with a second main body 521 and a second partition part 522. The second main body 521 is provided with a second upper surface 5211, a second lower surface 5212, and a second opening 5213. The second partition part 522 is connected to the second main body 521, and the second partition part 522 is configured for separating the second opening 5213 into a fourth adjustment hole 5214 and a fifth adjustment hole 5215. The eighth end 32 is provided with a sixth adjustment hole 321. The second tightening strap 22 is provided with a fifth end 221 and a sixth end 222. The second adjustment buckle 52 is positioned between the fifth end 221 and the sixth end 222. The fifth end 221 is connected to the second end 12. The sixth end 222 passes through the fourth adjustment hole 5214 from the second lower surface 5212 of the second main body 521 to enter the second upper surface 5211, then sequentially passes through the second partition part 522 and the fifth adjustment hole 5215 from the second upper surface 5211 to enter the second lower surface 5212, and finally sequentially passes through the sixth adjustment hole 321 and the second lower surface 5212 to connect with the second partition part 522, so that the second tightening strap 22 is slidable on the second partition part 522 to adjust a distance between the second end 12 and the eighth end 32, thereby adjusting the size of the tightening space 4. Through the above structure, the first tightening strap 21 is slidable on the first partition part 512 to adjust a distance between the first end 11 and the seventh end 31, thereby adjusting the size of the tightening space 4, and the second tightening strap 22 is slidable on the second partition part 522 to adjust the distance between the second end 12 and the eighth end 32, thereby adjusting the size of the tightening space 4. Therefore, the user can simultaneously adjust a length of the first tightening strap 21 and a length of the second tightening strap 22, thereby adjusting the size of the tightening space 4 to tighten the eyeshade on the user's head. Moreover, since the length of the first tightening strap 21 and the length of the second tightening strap 22 can be simultaneously adjusted, the flexible anti-slip pad body 3 can be adjusted to a position directly facing a center of the eyeshade main body 1, so that the flexible anti-slip pad body can fit the back of the user's head, thereby improving the wearing comfort of the eyeshade. The first adjustment buckle 51 and the second adjustment buckle 52 can be made of metal or plastic.

In this embodiment, the seventh end 31 is provided with a first convex lug part 312, and the eighth end 32 is provided with a second convex lug part 322. The third adjustment hole 311 is defined in the first convex lug part 312, and the sixth adjustment hole 321 is defined in the second convex lug part 322. Through the above structure, the design is reasonable, the structure is simple, and the connection is stable, effectively achieving the setting of the third adjustment hole 311 and the sixth adjustment hole 321.

Figure 10:
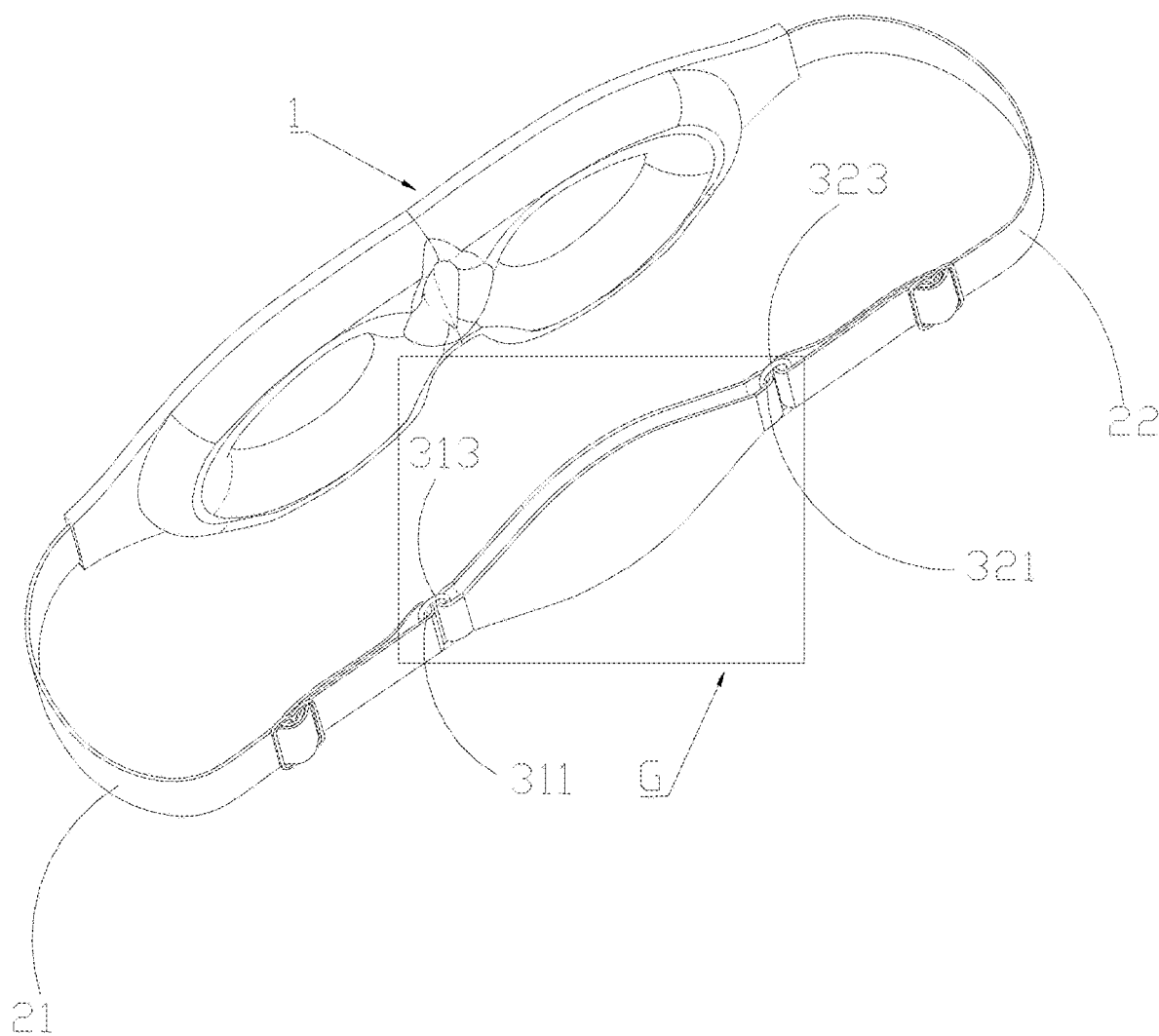
FIG. 10 is a schematic diagram of a structure of a first installation buckle and a second installation buckle.
Figure 11:
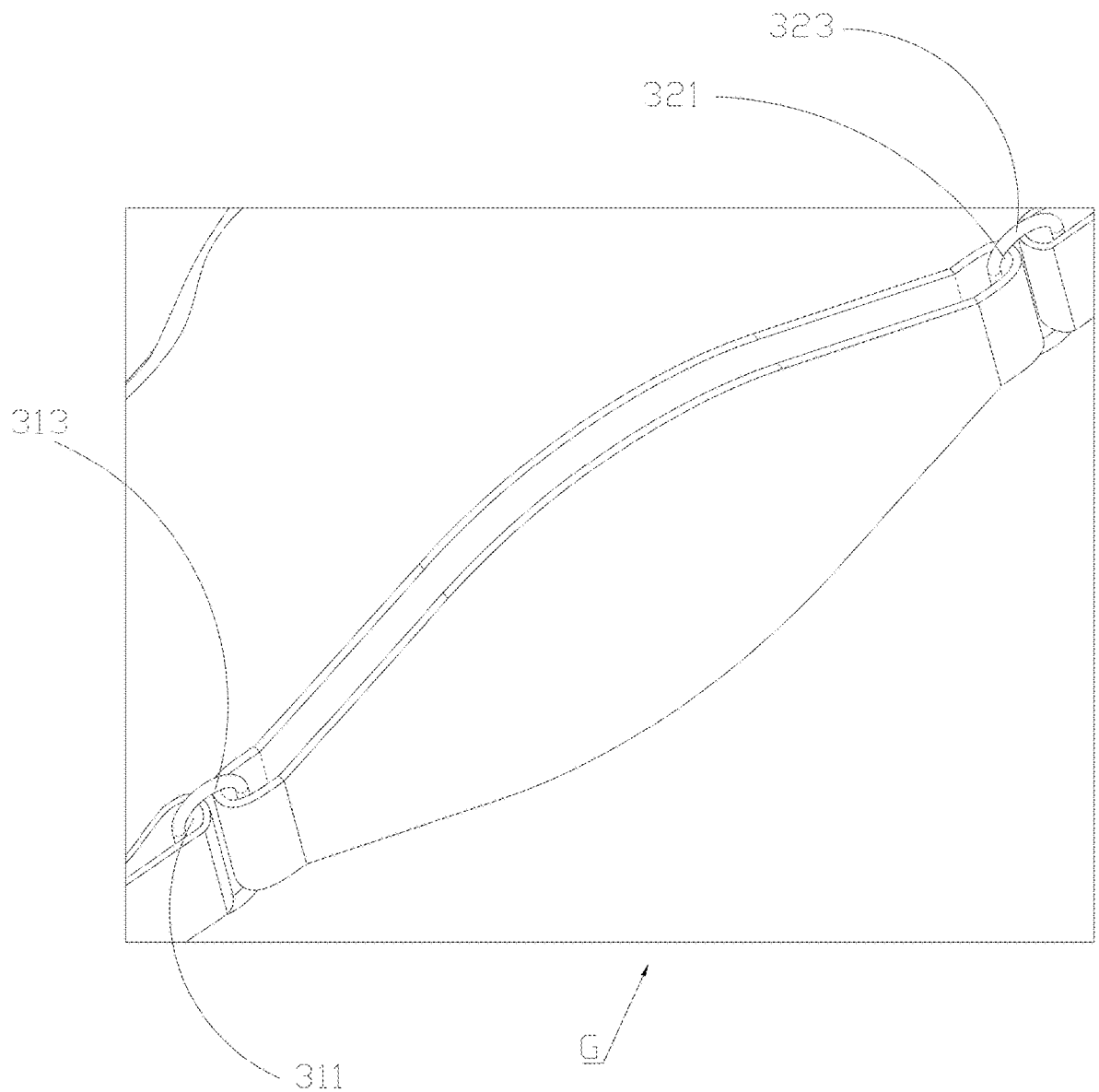
FIG. 11 is an enlarged view of area G in FIG. 10.

Referring to FIGS. 10-11, in some embodiments, the sleeping eyeshade further includes a first installation buckle 313 and a second installation buckle 323. The first installation buckle 313 is connected to the seventh end 31, and the second installation buckle 323 is connected to the eighth end 32. The third adjustment hole 311 is defined in the first installation buckle 313, and the sixth adjustment hole 321 is defined in the second installation buckle 323. The first installation buckle 313 and the second installation buckle 323 can be made of metal or plastic.

In this embodiment, the fourth end 212 is equipped with a first sleeving opening 2121. The first sleeving opening 2121 wraps the first partition part 512 to connect the fourth end 212 with the first partition part 512. The sixth end 222 is equipped with a second sleeving opening 2221. The second sleeving opening 2221 wraps the second partition part 522 to connect the sixth end 222 with the second partition part 522. Through the above structure, the design is reasonable, the structure is simple, and the connection is stable, effectively achieving the connection between the fourth end 212 and the first partition part 512, and the connection between the sixth end 222 and the second partition part 522. The fourth end 212 is bent and then connected to a side wall of the first tightening strap 21 to surround and form the first sleeving opening 2121. The sixth end 222 is bent and then connected to a side wall of the second tightening strap 22 to surround and form the second sleeving opening 2221.

In this embodiment, the first tightening strap 21 and the second tightening strap 22 extend longitudinally, and a transverse width of the flexible anti-slip pad body 3 is greater than a transverse width of the first tightening strap 21 and the second tightening strap 22. Through the above structure, by increasing an area of the flexible anti-slip pad body 3, a friction force between the flexible anti-slip pad body 3 and the head can be increased, thereby enhancing the tightening force of the tightening space 4, preventing the eyeshade from slipping off the user's head. Moreover, increasing the area of the flexible anti-slip pad body 3 can further reduce the pressure of the flexible anti-slip pad body 3 on the head, thereby improving the user's wearing comfort.

In this embodiment, the flexible anti-slip pad body 3 is made of Thermoplastic Elastomer (TPE). Through the above structure, the flexible TPE anti-slip pad body has high strength, high resilience, and can be produced by injection molding. The flexible TPE anti-slip pad body has a wide range of applications and is environmentally friendly, non-toxic, and safe. With good resilience and good fitting, the flexible TPE anti-slip pad body can better fit the user's head to prevent the eyeshade from slipping. The flexible anti-slip pad body 3 is a transparent flexible TPE anti-slip pad body.

In this embodiment, the flexible anti-slip pad body 3 is a flexible silicone anti-slip pad body. Through the above structure, the flexible silicone anti-slip pad body has high strength, high resilience, and can be produced by injection molding. The flexible silicone anti-slip pad body has a wide range of applications and is environmentally friendly, non-toxic, and safe. With good resilience and good fitting, the flexible silicone anti-slip pad body can better fit the user's head to prevent the eyeshade from slipping. The flexible anti-slip pad body 3 is a transparent flexible silicone anti-slip pad body.

In this embodiment, the flexible anti-slip pad body 3 is a flexible cloth anti-slip pad body.

In this embodiment, an inner side of the eyeshade main body 1 is provided with a first concavity 13 and a second concavity 14. The first concavity 13 and the second concavity 14 are respectively positioned on a left side and a right side of the eyeshade main body 1. The first concavity 13 and the second concavity 14 are configured for avoiding the user's eyes. Through the above structure, since the first concavity 13 and the second concavity 14 are configured for avoiding the user's eyes, the eyeshade main body 1 can better fit the user's face contour and prevent the eyeshade main body 1 from leaking light, thereby improving a light shading effect of the eyeshade main body 1.

The inner side of the eyeshade main body 1 is further provided with a third concavity 15. The third concavity 15 is positioned between the first concavity 13 and the second concavity 14. The third concavity 15 is configured for avoiding an area between eyebrows. Specifically, a lower side of the eyeshade main body 1 is further provided with a first avoidance gap 16. The first avoidance gap 16 is configured for avoiding a nose. Furthermore, a lower side of the third concavity 15 extends to the first avoidance gap 16, and the third concavity 15 is provided with a channel. The third concavity 15 is in communication with the first avoidance gap 16 through the channel. Through the above structure, since the third concavity 15 is configured for avoiding the area between the user's eyebrows, the eyeshade main body 1 can better fit the user's face contour and prevent light leakage from an upper side of the eyeshade main body 1, thereby improving the light shading effect of the eyeshade main body 1. Moreover, the lower side of the third concavity 15 extends to the first avoidance gap 16, the third concavity 15 is provided with the channel, and the third concavity 15 is in communication with the first avoidance gap 16 through the channel, allowing the eyeshade main body 1 to better fit the user's nose contour, preventing light leakage from the lower side of the eyeshade main body 1.

In this embodiment, the first end 11 of the eyeshade main body 1 is equipped with a third convex lug part 111, and the second end 12 of the eyeshade main body 1 is equipped with a fourth convex lug part 121. The third end 211 of the first tightening strap 21 is connected to the third convex lug part 111, and the fifth end 221 of the second tightening strap 22 is connected to the fourth convex lug part 121. The third end 211 is connected to the first end 11 by stitching, and the fifth end 221 is connected to the second end 12 by stitching. Specifically, the eyeshade main body 1 includes an outer layer 17, an inner layer 18, and a light shading filling layer 19. The outer layer 17 is connected to the inner layer 18, and an accommodating cavity 171 is formed between the inner layer 18 and the outer layer 17. The light shading filling layer 19 is positioned inside the accommodating cavity 171. Through the above structure, the first tightening strap 21 and the second tightening strap 22 are effectively connected to the eyeshade main body 1. Moreover, the light shading filling layer 19 is capable of improving the light shading performance of the eyeshade main body 1, thereby improving the user's sleep quality.

The above description only describes embodiments of the present disclosure, and is not intended to limit the present disclosure; various modifications and changes can be made to the present disclosure. Any modifications, equivalent substitutions, and improvements made within the spirit and scope of the present disclosure are intended to be included within the scope of the present disclosure.

What is claimed is:

1. A sleeping eyeshade comprising:
an eyeshade main body, the eyeshade main body being equipped with a first end and a second end;
an elastic tightening strap component, one end of the tightening strap component being connected to the first end, and an opposite end of the tightening strap component being connected to the second end; and
a flexible anti-slip pad body, the flexible anti-slip pad body being connected to the tightening strap component, and a tightening space being surrounded and formed among the flexible anti-slip pad body, the tightening strap component, and the eyeshade main body;
wherein the sleeping eyeshade further comprises an adjustment component, and the adjustment component is connected to the tightening strap component for adjusting a size of the tightening space;
wherein the tightening strap component comprises a first tightening strap and a second tightening strap, the flexible anti-slip pad body is equipped with a seventh end and an eighth end, the seventh end of the flexible anti-slip pad body is connected to the first end via the first tightening strap, and the eighth end of the flexible anti-slip pad body is connected to the second end via the second tightening strap;

wherein the adjustment component comprises a first adjustment buckle, the first adjustment buckle is provided with a first main body and a first partition part, and the first main body is provided with a first upper surface, a first lower surface and a first opening; the first partition part is connected to the first main body, the first partition part is configured for separating the first opening into a first adjustment hole and a second adjustment hole, and the seventh end is provided with a third adjustment hole; the first tightening strap is equipped with a third end and a fourth end, the first adjustment buckle is positioned between the third end and the fourth end, and the third end is connected to the first end; the fourth end passes through the first adjustment hole from the first lower surface of the first main body to enter the first upper surface, then sequentially passes through the first partition part and the second adjustment hole from the first upper surface to enter the first lower surface, and finally sequentially passes through the third adjustment hole and the first lower surface to connect with the first partition part, so that the first tightening strap is slidable on the first partition part to adjust a distance between the first end and the seventh end, thereby adjusting the size of the tightening space.

2. The sleeping eyeshade of claim 1, wherein the adjustment component comprises a second adjustment buckle, the second adjustment buckle is equipped with a second main body and a second partition part, and the second main body is provided with a second upper surface, a second lower surface and a second opening; the second partition part is connected to the second main body, the second partition part is configured for separating the second opening into a fourth adjustment hole and a fifth adjustment hole, and the eighth end is provided with a sixth adjustment hole; the second tightening strap is provided with a fifth end and a sixth end, the second adjustment buckle is positioned between the fifth end and the sixth end, and the fifth end is connected to the second end; the sixth end passes through the fourth adjustment hole from the second lower surface of the second main body to enter the second upper surface, then sequentially passes through the second partition part and the fifth adjustment hole from the second upper surface to enter the second lower surface, and finally sequentially passes through the sixth adjustment hole and the second lower surface to connect with the second partition part, so that the second tightening strap is slidable on the second partition part to adjust a distance between the second end and the eighth end, thereby adjusting the size of the tightening space.

3. The sleeping eyeshade of claim 2, wherein the seventh end is provided with a first convex lug part, the eighth end is provided with a second convex lug part, the third adjustment hole is defined in the first convex lug part, and the sixth adjustment hole is defined in the second convex lug part.

4. The sleeping eyeshade of claim 2, wherein the fourth end is equipped with a first sleeving opening, and the first sleeving opening wraps the first partition part to connect the fourth end with the first partition part; the sixth end is equipped with a second sleeving opening, and the second sleeving opening wraps the second partition part to connect the sixth end with the second partition part.

5. The sleeping eyeshade of claim 2, wherein the first end of the eyeshade main body is equipped with a third convex lug part, the second end of the eyeshade main body is equipped with a fourth convex lug part, the third end of the first tightening strap is connected to the third convex lug part, and the fifth end of the second tightening strap is connected to the fourth convex lug part.

6. The sleeping eyeshade of claim 2, wherein the third end is connected to the first end by stitching, and the fifth end is connected to the second end by stitching.

7. The sleeping eyeshade of claim 1, wherein the first tightening strap and the second tightening strap extend longitudinally, and a transverse width of the flexible anti-slip pad body is greater than a transverse width of the first tightening strap and the second tightening strap.

8. The sleeping eyeshade of claim 1, wherein the flexible anti-slip pad body is a flexible TPE anti-slip pad body.

9. The sleeping eyeshade of claim 1, wherein the flexible anti-slip pad body is a flexible silicone anti-slip pad body.

10. The sleeping eyeshade of claim 1, wherein the flexible anti-slip pad body is a flexible cloth anti-slip pad body.

11. The sleeping eyeshade of claim 1, wherein an inner side of the eyeshade main body is provided with a first concavity and a second concavity, the first concavity and the second concavity are respectively positioned on a left side and a right side of the eyeshade main body, and the first concavity and the second concavity are configured for avoiding a user's eyes.

12. The sleeping eyeshade of claim 11, wherein the inner side of the eyeshade main body is further provided with a third concavity, the third concavity is positioned between the first concavity and the second concavity, and the third concavity is configured for avoiding an area between eyebrows.

13. The sleeping eyeshade of claim 12, wherein a lower side of the eyeshade main body is further provided with a first avoidance gap, and the first avoidance gap is configured for avoiding a nose.

14. The sleeping eyeshade of claim 13, wherein a lower side of the third concavity extends to the first avoidance gap, the third concavity is provided with a channel, and the third concavity is in communication with the first avoidance gap through the channel.

15. The sleeping eyeshade of claim 1, wherein the eyeshade main body comprises an outer layer, an inner layer, and a light shading filling layer; the outer layer is connected to the inner layer, an accommodating cavity is formed between the inner layer and the outer layer, and the light shading filling layer is positioned inside the accommodating cavity.

* * * * *